United States Patent
Barney

[19]

[11] Patent Number: 6,024,713
[45] Date of Patent: Feb. 15, 2000

[54] LEG SUPPORT APPARATUS

[76] Inventor: George Melvin Barney, 3548 Golfing Green, Dallas, Tex. 75234

[21] Appl. No.: 09/213,516

[22] Filed: Dec. 17, 1998

[51] Int. Cl.⁷ ........................................................ A61F 5/00
[52] U.S. Cl. .................................. 602/23; 602/16; 602/26; 602/27
[58] Field of Search ................................ 602/16, 23, 26, 602/27, 28, 29; 623/33, 35

[56] References Cited

U.S. PATENT DOCUMENTS

| | | | |
|---|---|---|---|
| 2,558,986 | 7/1951 | Seelert | 128/80 |
| 3,928,872 | 12/1975 | Johnson | 2/22 |
| 4,456,003 | 6/1984 | Allard et al. | 128/80 |
| 4,494,534 | 1/1985 | Hutson | 128/80 |
| 4,602,627 | 7/1986 | Vito et al. | 128/80 |
| 4,688,559 | 8/1987 | Vito et al. | 128/80 |
| 4,856,500 | 8/1989 | Spademan | 128/80 |
| 4,967,734 | 11/1990 | Rennex | 128/80 |
| 5,002,045 | 3/1991 | Spademan | 128/80 |
| 5,242,378 | 9/1993 | Baker | 602/23 |
| 5,306,230 | 4/1994 | Bodine | 602/26 |
| 5,490,831 | 2/1996 | Myers et al. | 602/26 |

*Primary Examiner*—Richard J. Apley
*Assistant Examiner*—Jayne Saydah
*Attorney, Agent, or Firm*—W. Kirk McCord

[57] ABSTRACT

A leg support apparatus is comprised of a pair of upper frames and a pair of lower frames pivotally connected at respective pivot joints. The upper frames are connected to a circumferentially adjustable cuff, which is adapted to be wrapped around the thigh of a user. The lower frames are attachable to the user's footwear. When the apparatus is being worn by the user, the upper frames are positioned on laterally opposed sides of the user's thigh and the lower frames are positioned on laterally opposed sides of the user's calf. When the user is in a sitting position with his leg flexed, the pivot joints are anteriorly positioned with respect to his knee joint. When the user extends his leg and puts weight on his footwear, the pivot joints are moved posteriorly, which moves the upper frames upwardly toward the cuff and tightens the cuff around the thigh to prevent the cuff from slipping. The user's weight is transferred from the footwear upwardly through the lower and upper frames to the cuff, thereby relieving the ankle and knee joints from the stress of the user's weight.

20 Claims, 5 Drawing Sheets

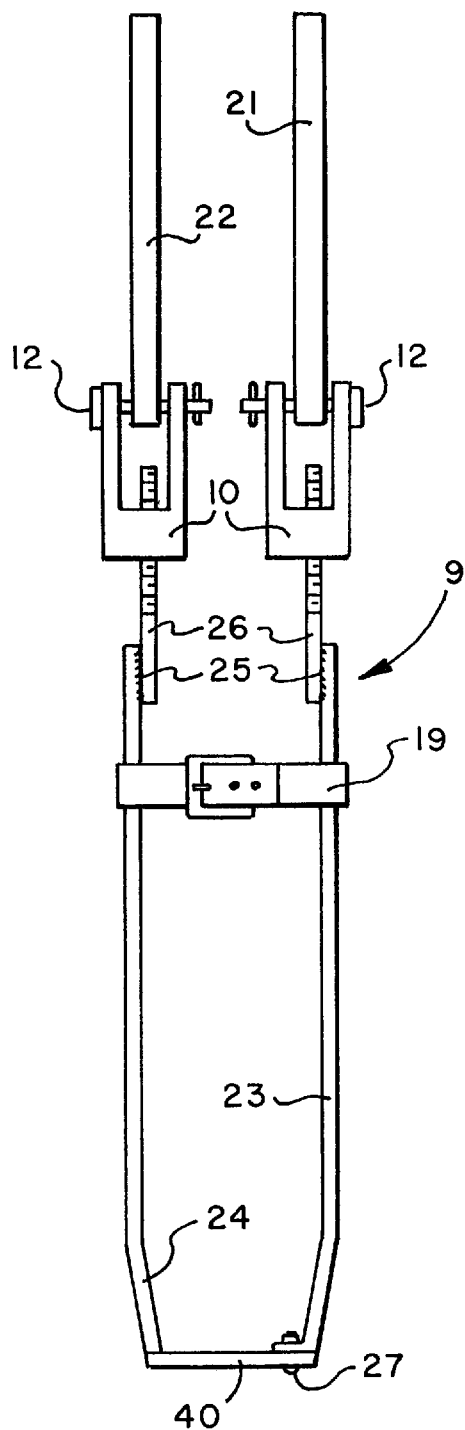
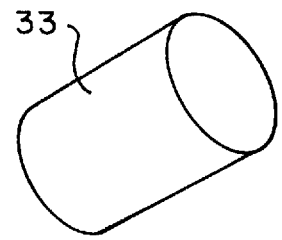
FIG. 5
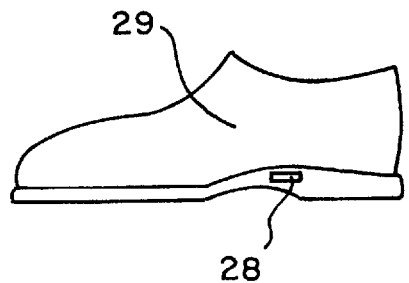
FIG. 4
FIG. 3

LEG SUPPORT APPARATUS

BACKGROUND OF THE INVENTION

1. Field of Invention

This invention relates to a leg support apparatus that when worn by a person helps prevent damage to knee and ankle cartilage.

2. Description of Related Art

It is known that over use of the knee and ankle through running and walking will wear down the cartilage. This will result in pain and swelling of the knee and ankle. Many devices are known in the art to help support a person's leg but none are suitable for protecting knee and ankle cartilage during exercise, such as walking or running.

Prior art leg support devices typically fall into four general categories: (1) leg position stabilizers (e.g., U.S. Pat. No. 4,494,534); (2) aids for handicapped persons (e.g., U.S. Pat. Nos. 4,688,559 and 4,602,627); (3) leg braces for bed ridden patients (e.g., U.S. Pat. No. 5,306,230); and (4) miscellaneous specialized devices for different activities such as skiing (e.g., U.S. Pat. No. 3,928,872).

U.S. Pat. No. 5,242,378 teaches a leg brace, the length of which is automatically adjustable during installation on a person's leg. U.S. Pat. Nos. 4,856,500 and 5,002,045 teach the use of an automatic circumference reducing cuff, which is actuated in response to certain leg movements.

SUMMARY OF THE INVENTION

In accordance with the present invention, leg support apparatus is provided, which is comprised of elongated upper and lower support members; a first securing member for securing the upper support member to a user's body above the knee; a second securing member for securing the lower support member to footwear on the user's foot; and a pivot joint intermediate the first and second securing members and pivotally connecting the upper and lower support members.

In accordance with a feature of the invention, a length adjustment member is provided to adjust the length of the apparatus so that the upper and lower support members have a greater cumulative length than a distance along the user's leg between the first and second securing members. When the apparatus is being worn by the user, the upper support member extends along the thigh portion of the user's leg and the lower support member extends along the calf portion of the user's leg. The pivot joint is positionable anteriorly offset with respect to the user's knee joint when the user's leg is flexed and is operable to move posteriorly when the leg is extended to move the upper and lower support members into substantial longitudinal alignment along the user's leg. Therefore, when body weight is placed on the user's foot, the upper support member is urged upwardly against the first securing member to transfer at least some of the body weight from the footwear upwardly through the second securing member and the support members to the first securing member. The ankle and knee joints are bypassed, thereby relieving stress on the ankle and knee cartilage.

In accordance with an embodiment of the invention, the first securing member is comprised of a circumferentially adjustable cuff member, which is positionable around the thigh portion of the user's leg. A circumferential adjustment member is operable to tighten the cuff member in response to upward movement of the upper support member, thereby preventing the cuff member from slipping on the user's leg.

In the preferred embodiment, the upper support member includes a pair of upper frames positionable on laterally opposed sides of the thigh portion of the user's leg and the lower support member includes a pair of lower frames positionable on laterally opposed sides of the calf portion of the user's leg. Two pivot joints are provided for pivotally connecting the lower frames to the upper frames. The pivot joints are positionable on laterally opposed sides of the user's leg, proximate to the knee joint.

The circumferential adjustment member preferably includes scissor means coupled between the cuff member and the upper frames. The scissor means is operable to close in response to upward movement of the upper frames to tighten the cuff member in pressure engagement with the thigh portion and to open in response to release of the pressure engagement. The cuff member preferably includes plural tapered members adapted to accommodate the contour of the thigh portion of the user's leg.

In accordance with the present invention, leg support apparatus is provided which helps protect ankle and knee cartilage during physical exercise without restricting the normal range of motion of the user's leg.

BRIEF DESCRIPTION OF THE DRAWINGS

The particular features and advantages of the invention will become apparent from the following description taken in connection with the accompanying drawings in which:

FIG. 3 is a front elevation view of the leg support apparatus;

FIG. 4 is a side elevation view of a shoe modified to receive the leg support apparatus of the present invention;

FIG. 5 is a perspective view of a thigh pad for use in connection with the leg support apparatus of the present invention;

DETAILED DESCRIPTION OF THE PREFERRED EMBODIMENT

Figure 1:
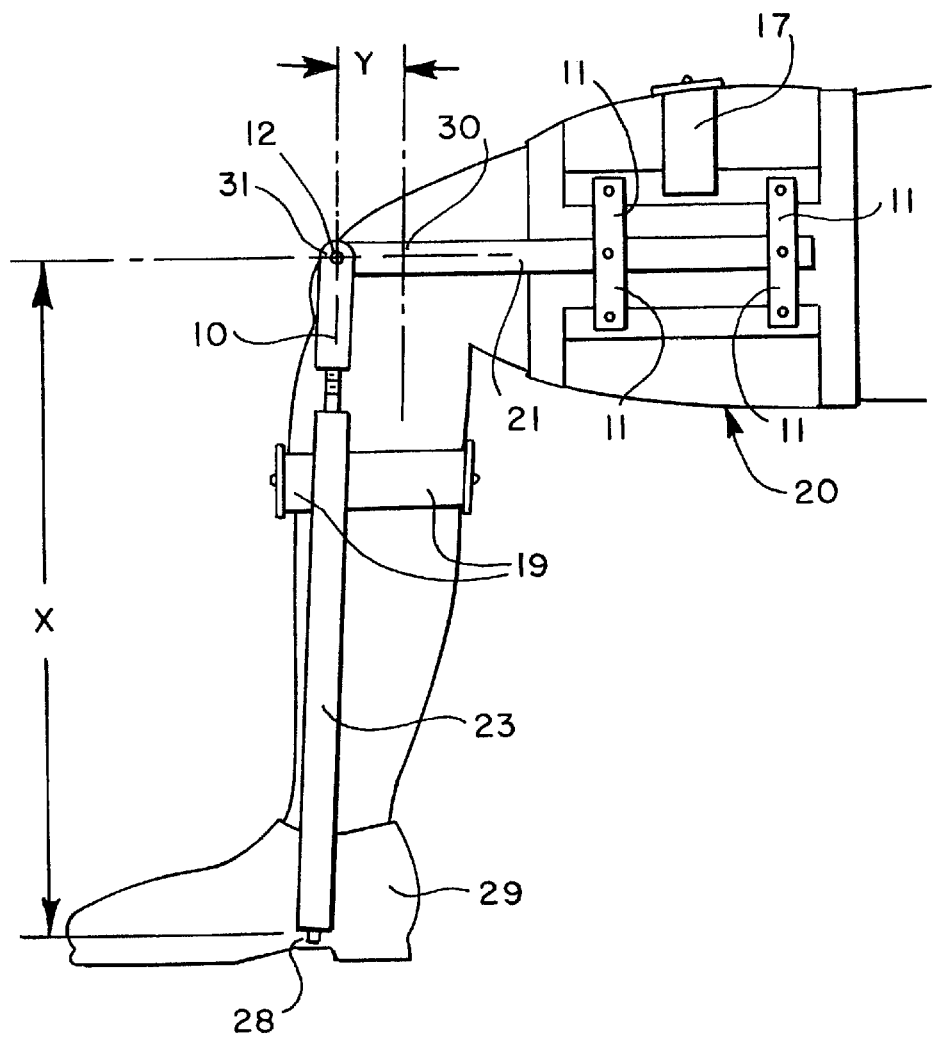
FIG. 1 is a side elevation view of a leg support apparatus according to the present invention, showing the apparatus being worn by a user with the user's leg in a flexed position.

Referring to FIGS. 1–8B, a leg-mountable apparatus 9 (FIG. 3), according to the present invention, provides knee and ankle support, while allowing normal operation of leg nerves, muscles, and bones when a user is standing, walking or running. The structure and operation of apparatus 9 will be described hereinafter with reference to only one leg of a user. One skilled in the art will understand and appreciate that apparatus 9 may be on either the right or left leg or on both legs.

Apparatus 9 includes upper and lower support members. Upper support member is comprised of parallel upper frames 21, 22 and lower support member is comprised of parallel lower frames 23, 24. A modified shoe 29 (FIG. 4) has a slot 28 cut through the sole thereof parallel to and directly below the ankle axis of the user's foot, to accommodate a cross-member 40, which projects from lower frame 24 (FIG. 3). Cross-member 40 is inserted through slot 28 and is connected to lower frame 23 with nut and bolt 27. A first securing member, preferably a circumferentially adjustable thigh-mountable cuff 20 (FIG. 7) is coupled to upper frames 21, 22, as will be described in greater detail hereinafter. Nut and bolt 27 act as a second securing member, to secure lower frames 23, 24 to shoe 29.

Threaded bolts 26 (FIGS. 3, 6C) are welded, as indicated at 25 (FIG. 3) to lower frames 23 and 24. Threaded bolts 26 mate with adjustable pivot yokes 10, providing an adjustment for the length of lower frames 23 and 24 to accommodate different leg lengths X (FIG. 1) below the knee. Adjustable calf belt 19 attaches to lower frames 23 and 24 at the calf level. Belt 19 is adjustable in the front and rear to properly position the lower frames 23 and 24 relative to the calf. Pivot and cotter pin assembly 12 (FIG. 6D) connects pivot yoke 10 (FIG. 6C) to upper frames 21 and 22 (FIG. 3). Body weight is transmitted through this connection when the user's foot is in contact with the ground.

Figures 2A, 2B:
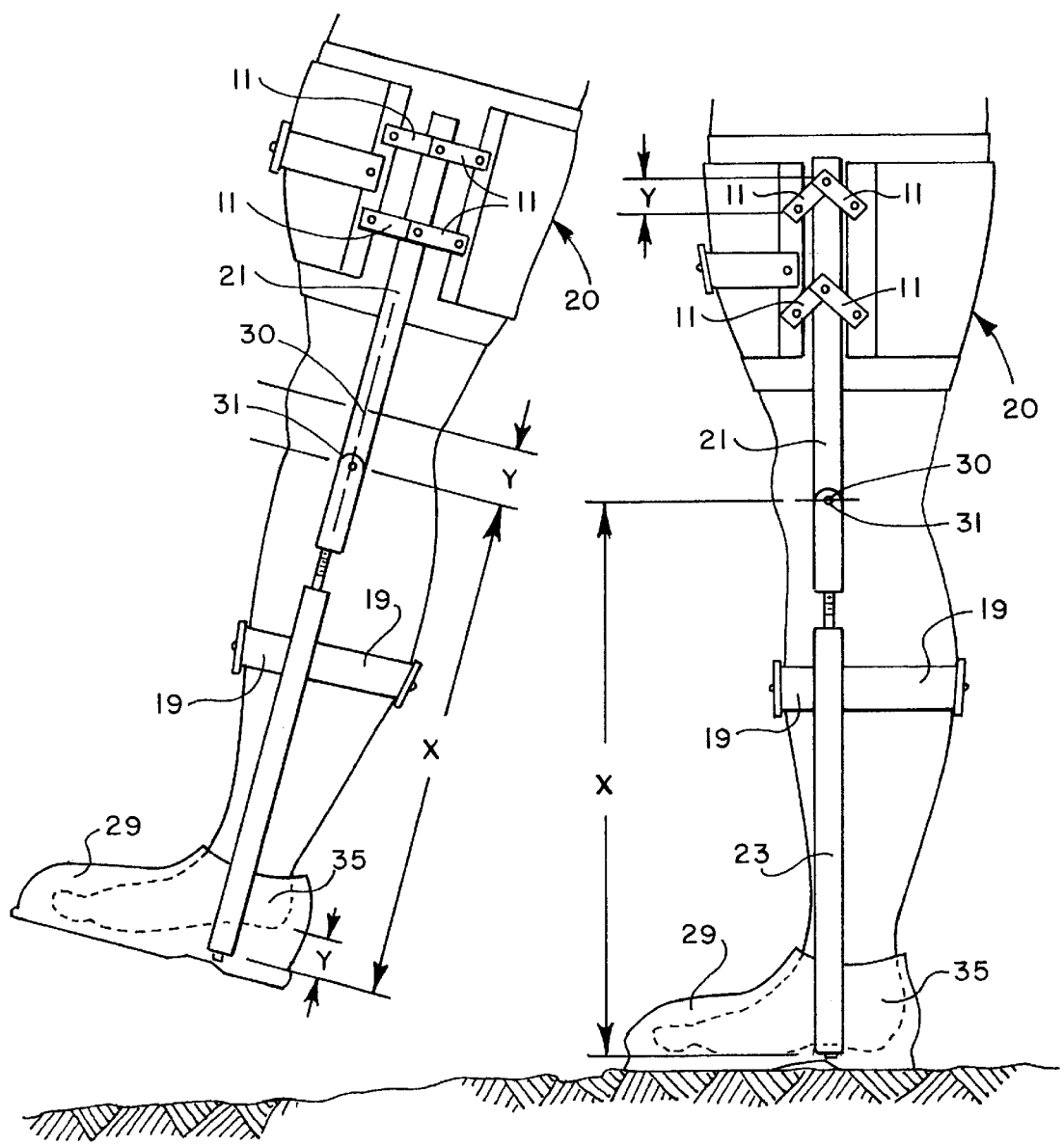
FIG. 2A is a side elevation view of the leg support apparatus being worn by a user, but with the user's leg extended and at least some of the user's body weight bearing on the foot.
FIG. 2B is a side elevation view of the leg support apparatus being worn by a user with the user's leg extended, but with no body weight on the foot.

Yoke 10 defines a pivot joint 31 (FIG. 1) which is located anteriorly of the user's knee joint 30 by a distance Y. When the leg is bent, as shown in FIG. 1, upper frames 21 and 22 are generally perpendicular to lower frames 23 and 24. As can be seen in FIG's 1, 2A and 2B, when the user moves from a sitting position wherein there is no substantial body weight bearing on the user's foot, as shown in FIG. 1, to an upright position wherein substantial body weight is bearing on the user's foot, as shown in FIG. 2A, upper frames 21, 22 and lower frames 23, 24 are displaced upwardly relative to cuff 20 (FIG. 2A) by a distance Y equal to the offset distance between knee joint 30 and pivot joint 31. This causes the body weight bearing on shoe 29 to be transmitted through lower frames 23, 24 and upper frames 21, 22 to cuff 20, thereby keeping weight off of the knee and ankle. In FIG. 2A the heel 35 of the user's foot is in contact with the heel portion of the shoe 29. When the leg is moved forward and the foot is off of the ground, as shown in FIG. 2B, tension on cuff 20 from the thigh causes cuff 20 to expand as a result of the scissor action of metal strips 11 coupled between portions 15 and 16 of cuff 20. This scissor action causes upper frames 21, 22 to move downwardly relative to the user's leg by a distance Y. Downward movement of upper frames 21, 22 causes lower frames 23, 24 to move the heel of shoe 29 a distance Y below the user's heel 35, so that the user's foot is effectively lifted up within shoe 29.

Figure 6A:
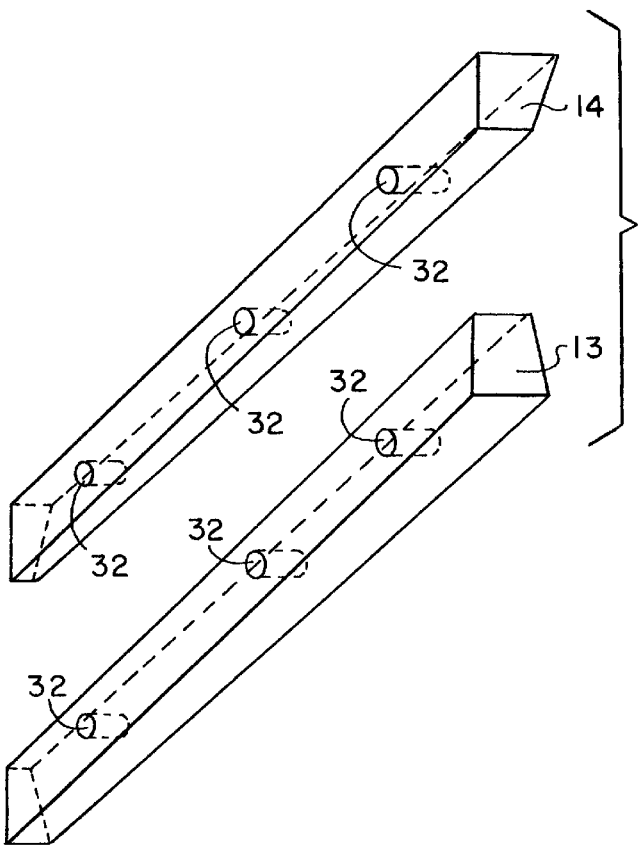
FIG. 6A is a perspective view of two tapered members used in the leg support apparatus of the present invention.
Figure 6B:
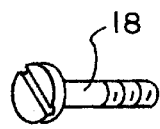
FIG. 6B is a perspective view of a metal screw used to attach components of the leg support apparatus of the present invention.
Figure 6D:
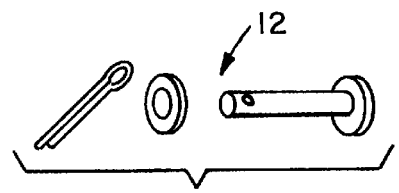
FIG. 6D is a perspective view of a pivot pin, washer and cotter pin used in the pivot joint referred to in the description of FIG. 6C hereinabove.
Figure 6C:
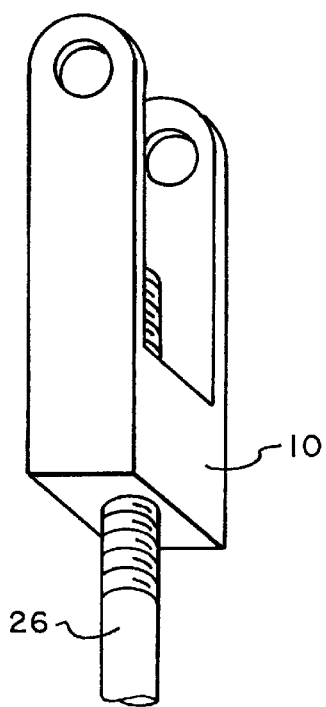
FIG. 6C is a perspective view of a portion of a pivot joint used to pivotally connect upper and lower portions of the leg support apparatus of the present invention.
Figure 6E:
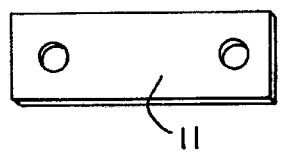
FIG. 6E is a perspective view of a scissor member used in the leg support apparatus of the present invention.
Figure 7:
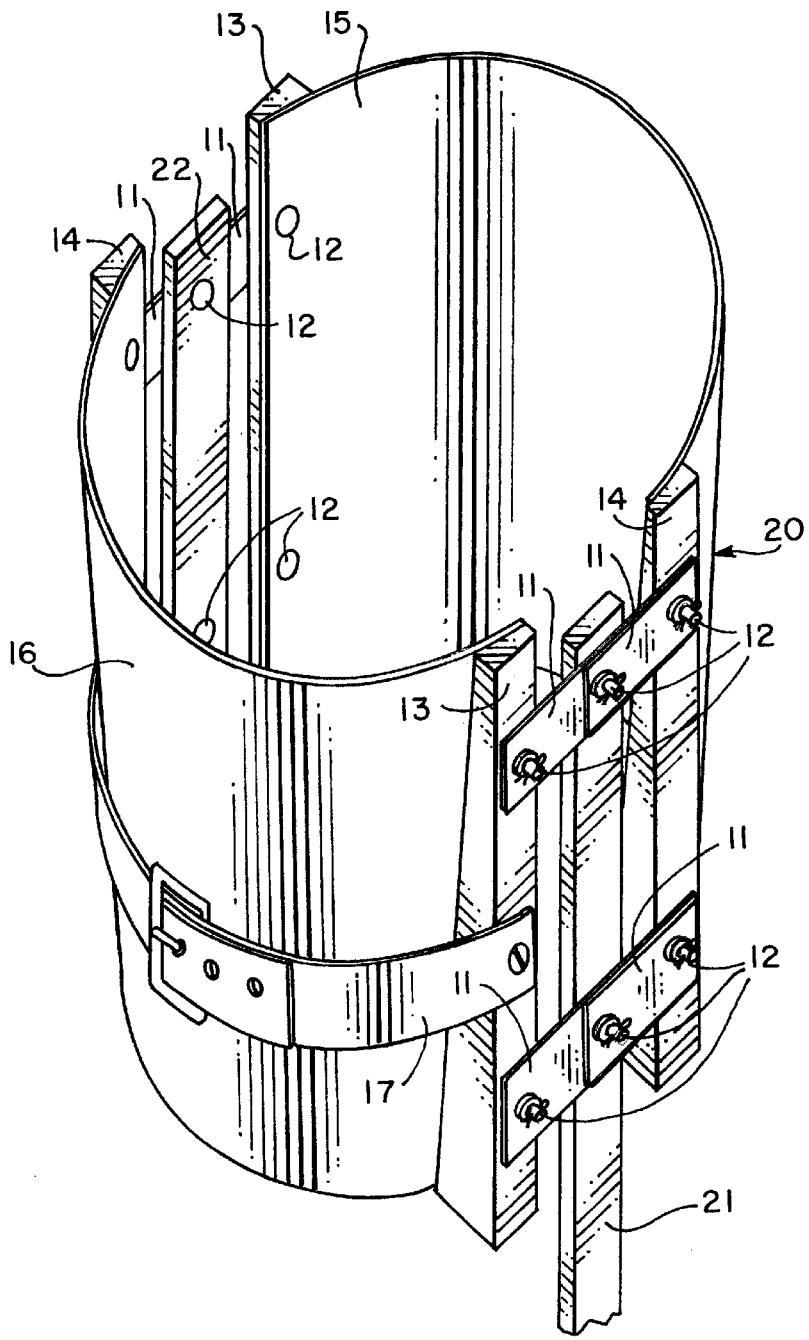
FIG. 7 is a perspective view of a cuff member used in the leg support apparatus of the present invention.
Figure 8A:
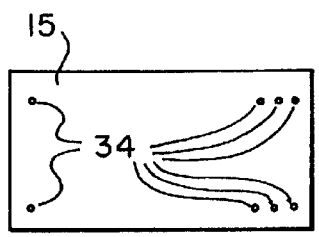
FIG. 8A is an elevation view of a flexible plastic sheet used in the cuff member referred to in the description of FIG. 7 hereinabove.
Figure 8B:
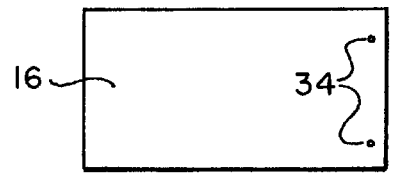
FIG. 8B is an elevation view of a second flexible plastic sheet used in the cuff member referred to in the description of FIG hereinabove.

Upper frames 21 22 are attached to cuff 20 by four sets of scissoring metal strips 11 (FIG. 6E), using pin assemblies 12 (FIG. 6D). Two sets of metal strips 11 are located on each side of the user's leg, as shown in FIG. 7. Each set of metal strips consists of two strips 11. As upper frames 21, 22 are urged upwardly as a result of the user's leg being extended and the user's weight being brought to bear on shoe 29 (FIG. 2A), the scissor action of metal strips 11 causes the circumference of cuff 20 to decrease so that it tightens around the user's leg and prevents cuff 20 from sliding up and down on the thigh.

As can be best seen in FIG. 7, cuff 20 includes two sets of double tapered metal blocks 13 and 14 (FIG. 6A), with opposite tapers so that they compensate for the taper of the thigh portion of the user's leg and position upper frames 21 and 22 so that they align with lower frames 23 and 24, when the leg is extended. Blocks 13 and 14 have holes 32 that accommodate pin assemblies 12 (FIG. 6D) to connect metal strips 11 (FIG. 6E) to blocks 13 and 14 and also to a first plastic sheet 15 (FIG. 8A) comprising a first portion of cuff 20. Sheet 15 has plural holes 34 for being aligned with corresponding holes 32 in blocks 13 and 14. Holes 32 are arranged to accommodate thighs of different sizes. Attachment members 12 are used to secure sheet 15 to blocks 13 and 14.

A second plastic sheet 16 (FIG. 8B) comprising a second portion of cuff 20 has two holes 34 that fit two corresponding holes 32 in double tapered block 13. Sheet 16 has sufficient length to reach around the leg and end under double tapered block 14 on an opposite side of the leg. One end of an adjustable cuff belt 17 (FIG. 7) is attached to block 13 with a threaded screw 18 (FIG. 6B), screwed into a hole 32. The other end of belt 17 is attached to block 14 on an opposite side of the leg, with a screw 18 screwed into a corresponding hole 32.

Belt 17 has a conventional buckle and may be adjusted by the wearer to achieve proper cuff tightness around the thigh. A commercially available leg pad 33 (FIG. 5) may be wrapped around the thigh under cuff 20 to prevent chafing during the use.

In order to use the leg support apparatus according to the present invention a person would need to make the following adjustments to fit the apparatus on his leg. In a sitting position, the user would separate upper frames 21 and 22 (FIG. 3) by removing the two pin assemblies 12 (FIG. 6D) from pivot yoke 10 (FIG. 3). Referring to FIG. 1, cuff 20 is positioned so that pivot holes in the bottom ends of upper frames 21 and 22 are at the same level X above the foot as the user's knee joint 30, and pivot joint 31 is positioned anteriorly with respect to knee joint 30 by a distance Y. Experience in the use of the invention will provide the needed information to optimally position the circumference reducing cuff 20 so that the distance between pivot joint 31 and knee joint 30 provides cartilage protection and a satisfactory level of comfort. Adjustment of the circumference of cuff 20 is accomplished by selecting a different set of holes 34 in sheet 15. By selecting the proper set of attachment holes 34 on sheet 15 and tightening belt 17, upper frames 21 and 22 are properly positioned on opposite sides of the leg.

When pivot joint 31 is in the proper position with respect to the knee joint 30, adjustment may be made to pivot yoke 10 and belt 19. Pivot yokes 10 on both sides of the leg are screwed up or down on threaded bolts 26 until the hole in pivot yoke 10 is in alignment with the pivot holes in upper frames 21 and 22. Coupling upper frames 21 and 22 may now be accomplished by reinstalling pin assemblies 12. Belt 19 may now be tightened to ensure that lower frames 23 and 24 will remain in the proper position.

The preferred embodiment of the invention has now been described in detail. Since changes in and modifications in the above-described details may be made without departing from the nature, spirit and scope of the invention, the invention is not to be limited to said details, but only by the appended claims and their equivalents.

I claim:

1. Leg support apparatus, comprising:

elongated upper and lower support members;

a first securing member comprising a circumferentially adjustable member for securing said upper support member to a user's body above the knee, whereby said upper support member is positionable to extend along the thigh portion of the user's leg;

a second securing member for securing said lower support member to footwear on the user's foot, whereby said lower support member is positionable to extend along the calf portion of the user's leg; and a pivot joint intermediate said first and second securing members and pivotally connecting said upper and lower support members;

a length adjustment member operable to adjust said apparatus longitudinally such that said upper and lower support members have a greater cumulative length than a distance along the user's leg between said first and second securing members and said pivot joint is anteriorly offset with respect to the user's knee joint when said apparatus is being worn by the user and the user's leg is flexed, said pivot joint being movable posteriorly in response to the user's leg being extended to move said upper and lower support members into substantially longitudinal alignment along the user's leg, such that when at least some of the user's weight is on the footwear said upper support member is urged upwardly against said first securing member to transfer at least some of the user's weight from the footwear upwardly through said second securing member, said lower support member and said upper support member to said first securing member.

2. Apparatus of claim 1 wherein said upper support member includes a pair of upper frames respectively positionable on laterally opposed sides of the thigh portion of the user's leg and said lower support member includes a pair of lower frames respectively positionable on laterally opposed sides of the calf portion of the user's leg, said pivot joint including first and second pivot joints, said first pivot joint pivotally connecting one of said upper frames and one of said lower frames and said second pivot joint pivotally connecting the other one of said upper frames and the other one of said lower frames, said first and second pivot joints being positionable on respective laterally opposed sides of the user's knee.

3. Apparatus of claim 2 wherein said first securing member is comprised of a cuff member positionable concentrically about the thigh portion of the user's leg, said cuff member including a pair of circumferential adjustment members respectively coupled to said pair of upper frames, said circumferential adjustment members being operable to reduce the circumference of said cuff member so as to tighten said cuff member around the thigh portion in response to said upper frames being urged upwardly, said upper frames being urged upwardly when the user's leg is extended and at least some of the user's weight is on the footwear, whereby said cuff member is secured in a relatively fixed position with respect to the user's leg by pressure engagement between said cuff member and the thigh portion and at least some of the user's weight is transferred from the footwear upwardly through said lower and upper frames to said cuff member, said circumferential adjustment members being further operable to allow the circumference of said cuff member to increase so as to release said pressure engagement in response to said upper frames not being urged upwardly.

4. Apparatus of claim 3 wherein each of said circumferential adjustment members is comprised of scissor means, said scissor means being closed in response to upward movement of said upper frames to tighten said cuff member and being opened in response to release of said pressure engagement.

5. Apparatus of claim 3 wherein said second securing member includes a mounting member adapted to be inserted through aligned openings in the sole of the user's footwear and means for attaching said mounting member to said lower frames, whereby said lower frames are securable to the user's footwear.

6. Apparatus of claim 2 further including a pair of length adjustment members respectively positionable on laterally opposed sides of the user's leg and being cooperable to adjust said apparatus.

7. Apparatus of claim 1 wherein said first securing member is comprised of a cuff member positionable concentrically about the thigh portion of the user's leg, said cuff member including a circumferential adjustment member coupled to said upper support member, said circumferential adjustment member being operable to reduce the circumference of said cuff member so as to tighten said cuff member about the thigh portion in response to said upper support member being urged upwardly, whereby said cuff member is secured in a relatively fixed position with respect to the user's leg by pressure engagement between said cuff member and said thigh portion and at least some of the user's weight is transferred from the footwear upwardly through said lower and upper support members to said cuff member, said circumferential adjustment member being further operable to allow the circumference of said cuff member to increase so as to release said pressure engagement in response to said upper support member not being urged upwardly.

8. Apparatus of claim 7 wherein said circumferential adjustment member is comprised of scissor means, said scissor means being closed in response to upward movement of said upper support member to tighten said cuff member and being opened in response to release of said pressure engagement.

9. Leg support apparatus, comprising:

elongated upper and lower support members;

a cuff member positionable concentrically about the thigh portion of a user's leg;

a circumferential adjustment member coupled between said cuff member and said upper support member;

a securing member for securing said lower support member to footwear on the user's foot;

a pivot joint pivotally connecting said upper and lower support members, said pivot joint being operable when said apparatus is being worn by the user to urge said upper support member upwardly in response to the user's leg being extended and at least some of the user's weight being on the footwear, said circumferential adjustment member being operable to reduce the circumference of said cuff member so as to tighten said cuff member about the thigh portion in response to said upper support member being urged upwardly, whereby said cuff member is secured in a relatively fixed position with respect to the user's leg by pressure engagement between said cuff member and the thigh portion and at least some of the user's weight is transferred from the footwear upwardly through said securing member, said lower support member and said upper support member to said cuff member.

10. Apparatus of claim 9 wherein said circumferential adjustment member is further operable to allow said upper support member to move downwardly when said apparatus is being worn by the user in response to the user's leg being extended and the user's footwear not bearing any of the user's weight, whereby said lower support member is moved downwardly along with said upper support member to extend the footwear away from the user's foot.

11. Apparatus of claim 9 wherein said circumferential adjustment member is comprised of scissor means, said scissor means being closed in response to upward movement of said upper support member to tighten said cuff member and being opened in response to release of said pressure engagement.

12. Apparatus of claim 9 wherein said upper support member includes a pair of upper frames respectively positionable on laterally opposed sides of the thigh portion of the user's leg and said lower support member includes a pair of lower frames respectively positionable on laterally opposed sides of the calf portion of the user's leg, said pivot joint including first and second pivot joints, said first pivot joint pivotally connecting one of said upper frames and one of said lower frames and said second pivot joint pivotally connecting the other one of said upper frames and the other one of said lower frames, said first and second pivot joints being positionable on respective laterally opposed sides of the user's knee.

13. Apparatus of claim 12 wherein said circumferential adjustment member includes a pair of circumferential adjustment members respectively coupled between said upper frames and said cuff member.

14. Apparatus of claim 13 wherein each of said circumferential adjustment members is comprised of scissor means, said scissor means being closed in response to upward movement of said upper frames to tighten said cuff member and being opened in response to release of said pressure engagement.

15. Apparatus of claim 12 wherein said securing member includes a mounting member adapted to be inserted through aligned openings in the sole of the user's footwear and means for attaching said mounting member to said lower frames, whereby said lower frames are securable to the user's footwear.

16. Apparatus of claim 9 wherein said circumferential adjustment member is comprised of scissor means, said scissor means being closed in response to upward movement of said upper support member to tighten said cuff and being opened in response to release of said pressure engagement.

17. Apparatus of claim 9 wherein said cuff member includes plural tapered members adapted to accommodate the contour of the thigh portion of the user's leg.

18. Apparatus of claim 17 wherein said cuff member including diametrically opposed first and second pairs of tapered members, said circumferential adjustment member includes first and second adjustment members respectively coupled to said first and second pairs of tapered members.

19. A method of supporting a person's leg, comprising the steps of:

providing a support device having elongated upper and lower support members and a pivot joint pivotally connecting said upper and lower support members;

securing said upper support member to the person's body above the knee, so that said upper support member extends along the thigh portion of the person's leg;

securing said lower support member to footwear on the person's foot, so that said lower support member extends along the calf portion of the person's leg;

adjusting said device longitudinally such that said upper and lower support members have greater cumulative length then the user's leg between where the upper support member is secured to a person's body above the knee and where the lower support member is secured to the footwear and so that said pivot joint is anteriorly offset with respect to the person's knee joint when the person's leg is flexed; and allowing said pivot joint to move posteriorly in response to the person's leg being extended and at least some of the user's weight being on the footwear so that said upper support member is urged upwardly to transfer at least some of the person's weight from the footwear upwardly through said lower support member and said upper support member to the person's body above the knee, whereby the person's knee and ankle are supported.

20. The method of claim 19 wherein said providing further includes providing a circumferentially adjustable cuff member and said securing said upper support member includes securing said cuff member to said upper support member and positioning said cuff member concentrically about the thigh portion of the person's leg, said allowing further including allowing said cuff member to tighten about the thigh portion in response to upward movement of said upper support member when the person's leg is extended and the footwear is in contact with a support surface, whereby at least some of the person's weight is transferred from the footwear upwardly through said lower support member and said upper support member to said cuff member.

* * * * *